United States Patent
Ebert et al.

(10) Patent No.: US 9,932,293 B2
(45) Date of Patent: Apr. 3, 2018

(54) ETHERAMINES BASED ON ALKOXYLATED GLYCERINE OR TRIMETHYLOLPROPANE

(71) Applicant: BASF SE, Ludwigshafen (DE)

(72) Inventors: Sophia Ebert, Mannheim (DE); Björn Ludolph, Ludwigshafen (DE); Christof W. Wigbers, Mannheim (DE); Steffen Maas, Bubenheim (DE); Dieter Boeckh, Limburgerhof (DE); Frank Huelskoetter, Bad Dükheim (DE); Brian J. Loughnane, Fairfield, OH (US); Amy Eichstadt Waun, West Chester, OH (US); Kevin Christmas, Mason, OH (US); Darren Rees, Newcastle upon Tyne (GB); Stefano Scialla, Rome (IT)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 14/913,840

(22) PCT Filed: Jul. 15, 2014

(86) PCT No.: PCT/EP2014/065114
§ 371 (c)(1),
(2) Date: Feb. 23, 2016

(87) PCT Pub. No.: WO2015/028193
PCT Pub. Date: Mar. 5, 2015

(65) Prior Publication Data
US 2016/0251304 A1   Sep. 1, 2016

(30) Foreign Application Priority Data
Aug. 26, 2013 (EP) ..................... 13181700

(51) Int. Cl.
| | | |
|---|---|---|
| C07C 213/00 | (2006.01) |
| C07C 213/02 | (2006.01) |
| C07C 217/08 | (2006.01) |
| C11D 1/44 | (2006.01) |
| C11D 3/30 | (2006.01) |
| A61K 8/45 | (2006.01) |
| A61Q 5/02 | (2006.01) |
| A61Q 19/10 | (2006.01) |
| C08G 18/50 | (2006.01) |
| C08G 69/00 | (2006.01) |
| A61K 8/04 | (2006.01) |

(52) U.S. Cl.
CPC ............. C07C 213/02 (2013.01); A61K 8/45 (2013.01); A61Q 5/02 (2013.01); A61Q 19/10 (2013.01); C07C 217/08 (2013.01); C08G 18/5024 (2013.01); C08G 69/00 (2013.01); C11D 1/44 (2013.01); C11D 3/30 (2013.01)

(58) Field of Classification Search
CPC .................................................. C07C 213/00
USPC ........................................................ 528/412
See application file for complete search history.

(56) References Cited

U.S. PATENT DOCUMENTS

| | | |
|---|---|---|
| 3,654,370 A | 4/1972 | Yeakey |
| 4,609,683 A | 9/1986 | Grigsby, Jr. et al. |
| 5,403,509 A | 4/1995 | Pujol et al. |
| 5,530,127 A | 6/1996 | Reif et al. |
| 8,318,982 B2 | 11/2012 | Kubanek et al. |
| 8,487,135 B2 | 7/2013 | Kubanek et al. |
| 8,754,027 B2 | 6/2014 | Dobrawa et al. |
| 8,877,977 B2 | 11/2014 | Strautmann et al. |
| 9,068,147 B2 | 6/2015 | Dobrawa et al. |
| 2005/0234216 A1 | 10/2005 | Klein et al. |
| 2009/0124529 A1 | 5/2009 | Danziger et al. |
| 2014/0288265 A1 | 9/2014 | Ebert et al. |
| 2014/0305339 A1 | 10/2014 | Strautmann et al. |
| 2015/0057212 A1 | 2/2015 | Hulskotter et al. |
| 2015/0057213 A1 | 2/2015 | Hulskotter et al. |

(Continued)

FOREIGN PATENT DOCUMENTS

| | | |
|---|---|---|
| DE | 1 643 426 A1 | 3/1972 |
| EP | 0356047 A2 | 2/1990 |

(Continued)

OTHER PUBLICATIONS

U.S. Appl. No. 14/914,027, filed Feb. 24, 2016, Ebert et al.

(Continued)

*Primary Examiner* — Duc Truong
(74) *Attorney, Agent, or Firm* — Drinker Biddle & Reath LLP

(57) ABSTRACT

This invention relates to an etheramine of formula (I) based on glycerine or trimethylolpropane and its manufacturing process,

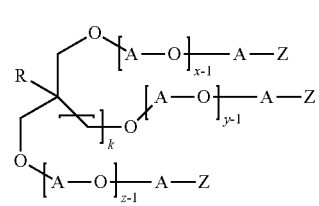

Formula (I)

wherein
R=H or ethyl, k=0 or 1
A represents a linear or branched alkylene group having $C_2$-$C_{18}$ carbon atoms,
A may be the same as or different from one another,
at least one A represents a linear or branched $C_4$-alkylene group,
the sum of x, y and z lies in the range of 3 to 100,
$x \geq y \geq 1$ and $z \geq 1$,
Z=NH2 or OH but at least two Z per molecule are NH2.

14 Claims, No Drawings

(56) References Cited

U.S. PATENT DOCUMENTS

2015/0361379 A1   12/2015  Hueffer et al.
2016/0002572 A1   1/2016   Ebert et al.
2016/0052867 A1   2/2016   Ebert et al.

FOREIGN PATENT DOCUMENTS

| EP | 696572 A1 | 2/1996 |
| EP | 1502913 A1 | 2/2005 |
| GB | 1185239 A | 3/1970 |
| JP | 2013194022 A | 9/2013 |
| WO | WO-0176729 A2 | 10/2001 |
| WO | WO-2011/067199 A1 | 6/2011 |
| WO | WO-2011/067200 A1 | 6/2011 |

OTHER PUBLICATIONS

European Search Report fpr EP13181700.9 dated Feb. 24, 2014.
International Search Report for PCT/EP2014/065114 dated Sep. 29, 2014.

ETHERAMINES BASED ON ALKOXYLATED GLYCERINE OR TRIMETHYLOLPROPANE

CROSS-REFERENCE TO RELATED APPLICATIONS

This application is a national stage application (under 35 U.S.C. § 371) of PCT/EP2014/065114, filed Jul. 15, 2014, which claims benefit of European Application No. 13181700.9, filed Aug. 26, 2013, both of which are incorporated herein by reference in their entirety.

This invention relates to etheramines based on glycerine or trimethylolpropane, wherein the etheramines contain at least one linear or branched $C_4$-alkylene group.

Due to the increasing popularity of easy-care fabrics made of synthetic fibers as well as the ever increasing energy costs and growing ecological concerns of detergent users, the once popular hot water wash has now taken a back seat to washing fabrics in cold water. Many commercially available laundry detergents are even advertised as being suitable for washing fabrics at 40° C. or 30° C. or even at room temperature. To achieve satisfactory washing result at such low temperatures, results comparable to those obtained with hot water washes, the demands on low-temperature detergents are especially high.

It is known to include certain additives in detergent compositions to enhance the detergent power of conventional surfactants so as to improve the removal of grease stains at temperatures of 60° C. and below.

There is also a continuous need for cleaning compositions that remove grease stains from fabrics and other soiled materials, as grease stains are challenging stains to remove. Conventional cleaning compositions directed to grease removal frequently utilize various amine compounds which tend to show strong negative impacts on whiteness. As a consequence there is still a continual need for improved amine compositions which provide improved grease removal from fabrics and other soiled materials and at the same time do not negatively impact the clay cleaning. These amine compositions should also have a suitable toxicological profile so that they can be used in household applications.

DE 1 643 426 A1 reads on a process for the manufacture of a polyoxyalkylene polyamine wherein a polyalcohol with 3 to 8 hydroxyl groups is reacted with C1-C18 alkyleneoxide and afterwards aminated in the presence of a catalyst.

EP 1 502 913 A1 describes a process for producing polyoxyalkylene triamine by bringing a polyoxyalkylene triol into contact with ammonia and hydrogen in the presence of a catalyst. The polyoxyalkylene triol contains alkylene groups having 2 to 6 carbon atoms.

WO 01/76729 A2 relates to a composition comprising a multifunctional polyetheramine with at least two amine groups per molecule, wherein the polyetheramine contains alkylene groups having 2 and 3 carbon atoms.

U.S. Pat. No. 4,609,683 describes a quasi-propolymer prepared by the reaction of aromatic isocyanates with polyoxyalkylene triamines and an isatoic anhydride.

It was an object of the present invention to provide compounds which would improve the washing performance of detergents at low temperatures, i.e. at temperatures as low as 30° C. or even lower.

This goal was achieved with an etheramine of formula (I),

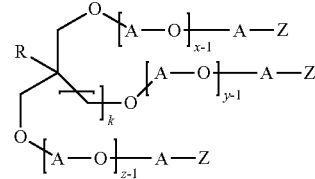

Formula (I)

wherein
R=H or ethyl, k=0 or 1
A represents a linear or branched alkylene group having C2-C18 carbon atoms,
A may be the same as or different from one another,
at least one A represents a linear or branched $C_4$-alkylene group,
the sum of x, y and z lies in the range of 3 to 100,
$x \geq 1$, $y \geq 1$ and $z \geq 1$, Z=NH2 or OH but at least two Z per molecule are NH2, preferably Z is NH2

In a preferred embodiment at least three A represent a linear or branched $C_4$-alkylene group, in another preferred embodiment all A groups represent a linear or branched $C_4$-alkylene group.

Preferably the sum of x, y and z lies in the range of 3 to 30, even more preferably in the range of 3 to 10 and even more preferably in the range of 5 to 10.

The etheramine of formula (I) is obtained by a process comprising the following steps:
a) reacting glycerine or 1,1,1-trimethylolpropane with $C_4$-alkylene oxide and optionally with $C_2$-$C_{18}$ alkylene oxide, wherein the molar ratio of glycerine to $C_4$ alkylene oxide is in the range of 1:3 to 1:10,
b) aminating the alkoxylated glycerine with ammonia.

Alkoxylation

In a preferred embodiment the molar ratio of glycerine or 1,1,1-trimethylolpropane to $C_2$-$C_{18}$ alkylene oxide and in particular of butylene oxide is in the range of 1:3 to 1:6.

Alkoxylated triols are obtained by reaction of glycerine or 1,1,1-trimethylolpropane with alkylene oxides and can be affected according to general alkoxylation procedures known in the art.

The alkoxylated glycerine or 1,1,1-trimethylolpropane may be prepared in a known manner by reaction of glycerine or 1,1,1-trimethylolpropane with alkylene oxides. Suitable alkylene oxides are $C_2$-$C_{18}$ alkylene oxides like ethylene oxide, propylene oxide, butylene oxide, pentene oxide, hexene oxide, decene oxide, dodecene oxide etc.

Preferably the C2-C18 alkylene oxide is ethylene oxide, propylene oxide or a mixture thereof.

The glycerine or 1,1,1-trimethylolpropane are reacted with one single alkylene oxide or combinations of two or more different alkylene oxides. Using two or more different alkylene oxides, the resulting alkoxylate can be obtained as a block-wise structure or a random structure.

The molar ratio of glycerine or 1,1,1-trimethylolpropane to $C_4$-alkylene oxide and optionally $C_2$-$C_{18}$ alkylene oxides at which the alkoxylation reaction is carried out lies in the range of 1:3 to 1:10, preferably in the range of 1:3 to 1:6. In another embodiment, the molar ratio of glycerine or 1,1,1-trimethylolpropane to $C_4$-alkylene oxide and optionally $C_2$-$C_{18}$ alkylene oxides at which the alkoxylation reaction is carried out lies in the range of 1:5 to 1:10.

This reaction is undertaken generally in the presence of a catalyst in an aqueous solution at a reaction temperature from about 70 to about 200° C. and preferably from about 80 to about 160° C. This reaction may be affected at a pressure of up to about 10 bar, and in particular up to about 8 bar.

Examples of suitable catalysts are basic catalysts such as alkali metal and alkaline earth metal hydroxides such as sodium hydroxide, potassium hydroxide and calcium hydroxide, alkali metal alkoxides, in particular sodium and potassium $C_1$-$C_4$-alkoxides, such as sodium methoxide, sodium ethoxide and potassium tert-butoxide, alkali metal and alkaline earth metal hydrides such as sodium hydride and calcium hydride, and alkali metal carbonates such as sodium carbonate and potassium carbonate. Preference is given to alkali metal hydroxides, particular preference being given to potassium hydroxide and sodium hydroxide. Typical use amounts for the base are from 0.05 to 10% by weight, in particular from 0.1 to 2% by weight, based on the total amount of polyalkyleneimine and alkylene oxide.

Amination

The amination is carried out in the presence of copper-, nickel- or cobalt-containing catalyst.

The catalytically active material of the catalysts, before the reduction thereof with hydrogen, comprises oxygen compounds of aluminum, of copper, of nickel and of cobalt, and is in the range from 0.2 to 5.0% by weight of oxygen compounds of tin, calculated as SnO.

Etheramines according to Formula (I) are obtained by reductive amination of the alkoxylated glycerine or 1,1,1-trimethylolpropane with ammonia in presence of hydrogen and a catalyst containing nickel. Suitable catalysts are described in WO 2011/067199 A1 and in WO02011/067200 A1, and in EP0696572 B1. Preferred catalysts are supported copper-, nickel- and cobalt-containing catalysts, wherein the catalytically active material of the catalysts, before the reduction thereof with hydrogen, comprises oxygen compounds of aluminium, of copper, of nickel and of cobalt, and in the range from 0.2 to 5.0% by weight of oxygen compounds of tin, calculated as SnO. Other preferred catalysts are supported copper-, nickel- and cobalt-containing catalysts, wherein the catalytically active material of the catalysts, before the reduction thereof with hydrogen, comprises oxygen compounds of aluminium, of copper, of nickel, of cobalt and of tin, and in the range from 0.2 to 5.0% by weight of oxygen compounds of yttrium, of lanthanum, of cerium and/or of hafnium, each calculated as $Y_2O_3$, $La_2O_3$, $Ce_2O_3$ and $Hf_2O_3$ respectively. Another preferred catalyst is a zirconium, copper, nickel catalyst, wherein the catalytically active composition comprises from 20 to 85% by weight of oxygen-containing zirconium compounds, calculated as $ZrO_2$, from 1 to 30% by weight of oxygen-containing compounds of copper, calculated as CuO, from 30 to 70% by weight of oxygen-containing compounds of nickel, calculated as NiO, from 0.1 to 5% by weight of oxygen-containing compounds of aluminium and/or manganese, calculated as $Al_2O_3$ and $MnO_2$ respectively.

For the reductive amination step as well supported as non-supported catalyst can be used. The supported catalyst e.g. is obtained by deposition of the metallic components of the catalyst compositions onto support materials known to those skilled in the art, using techniques that are well-known in the art including without limitation, known forms of alumina, silica, charcoal, carbon, graphite, clays, mordenites; and molecular sieves, to provide supported catalysts as well. When the catalyst is supported, the support particles of the catalyst may have any geometric shape, for example the shape of spheres, tablets or cylinders in a regular or irregular version. The process can be carried out in a continuous or discontinuous mode, e.g. in an autoclave, tube reactor or fixed-bed reactor. The reactor design is also not narrowly critical. The feed thereto may be upflowing or downflowing, and design features in the reactor which optimize plug flow in the reactor may be employed.

By-products which contain secondary or tertiary amino functions may be formed under amination reaction conditions. Secondary amines are e.g. obtained from a reaction of a fully or partially aminated diol with another fully and/or partially aminated diol. Tertiary amines are formed e.g. via a reaction of a secondary amine with another fully or partially aminated diol.

The degree of amination is between 67 to 100% and most preferably from 85 to 100%. The degree of amination is calculated from the total amine value (AZ) divided by sum of the total acetylables value (AC) and tertiary amine value (tert. AZ) and multiplicated by 100 (Total AZ x100/(AC+tert. ZD).

The total amine value (AZ) is determined according to DIN 16945.

The total acetylables value (AC) is determined according to DIN 53240.

The secondary and tertiary amine are determined according to ASTM D2074-07.

The hydroxyl value is calculated from (total acetylables value+tertiary amine value)−total amine value.

In another preferred embodiment, the etheramines of the invention can also be further reacted with an acid. The acid may be selected from the group consisting of citric acid, lactic acid, sulfuric acid, methanesulfonic acid, hydrogen chloride, phosphoric acid, formic acid, acetic acid, propionic acid, valeric acid, oxalic acid, succinic acid, adipic acid, sebacic acid, glutaric acid, glucaric acid, tartaric acid, malic acid, benzoic acid, salicylic acid, phthalic acid, oleic acid, stearic acid and mixtures thereof. In an alternative embodiment, the etheramines of the invention may, in protonated form, have a surfactant as a counter ion, as obtained from e.g. linear alkyl benzene sulphonic acid.

Applications:

The inventive etheramine mixtures may be used in personal care, especially in shampoo and body wash formulations as well as in cleaning compositions.

They may also be used as curing agent for epoxy resins or as a reactant in the production of polymers but also in polyurethanes, polyureas, epoxy resins, polyamides.

The inventive etheramines have proved to be effective for removal of stains, particularly grease, from soiled material. Cleaning compositions with inventive etheramines also do not have the cleaning negatives seen with conventional, amine cleaning compositions for hydrophilic bleachable stains, such as coffee, tea, wine, or particulates. Additionally, for stain removal from white fabric, cleaning compositions with inventive etheramines do not cause the whiteness negatives that commercially available, amine cleaning compositions cause.

A further advantage of cleaning compositions comprising the inventive etheramines is their ability to remove grease stains in cold water cleaning solutions followed by cold water washing. Without being limited by theory, cold water solutions have the effect of causing greases to harden or solidify, making greases more resistant to removal, especially from fabric. Cleaning compositions with etheramine mixtures according to Formula (I), however, are surprisingly effective when used in cold water cleaning.

As used herein the phrase "cleaning composition" includes compositions and formulations designed for cleaning soiled material. Such compositions include but are not limited to, laundry cleaning compositions and detergents, fabric softening compositions, fabric enhancing compositions, fabric freshening compositions, laundry prewash, laundry pretreat, laundry additives, spray products, dry cleaning agent or composition, laundry rinse additive, wash additive, post-rinse fabric treatment, ironing aid, unit dose formulation, delayed delivery formulation, liquid hand dishwashing composition, detergent contained on or in a porous substrate or nonwoven sheet, automatic dish-washing agent, hard surface cleaner, and other suitable forms that may be apparent to one skilled in the art in view of the teachings herein. Such compositions may be used as a pre-laundering treatment, a post-laundering treatment, may be added during the rinse or wash cycle of the laundering operation, or used in homecare cleaning applications. The cleaning compositions may have a form selected from liquid, powder, single-phase or multi-phase unit dose, pouch, tablet, gel, paste, bar, or flake.

The cleaning compositions described herein may include from about 0.1% to about 10%, in some examples, from about 0.2% to about 5%, and in other examples, from about 0.5% to about 3%, by weight the composition, of an etheramine of Formula I.

Surfactant System

The cleaning compositions comprise a surfactant system in an amount sufficient to provide desired cleaning properties. In some embodiments, the cleaning composition comprises, by weight of the composition, from about 1% to about 70% of a surfactant system. In other embodiments, the liquid cleaning composition comprises, by weight of the composition, from about 2% to about 60% of the surfactant system. In further embodiments, the cleaning composition comprises, by weight of the composition, from about 5% to about 30% of the surfactant system. The surfactant system may comprise a detersive surfactant selected from anionic surfactants, nonionic surfactants, cationic surfactants, zwitterionic surfactants, amphoteric surfactants, ampholytic surfactants, and mixtures thereof. Those of ordinary skill in the art will understand that a detersive surfactant encompasses any surfactant or mixture of surfactants that provide cleaning, stain removing, or laundering benefit to soiled material.

Adjunct Cleaning Additives

The cleaning compositions of the invention may also contain adjunct cleaning additives. Suitable adjunct cleaning additives include builders, structurants or thickeners, clay soil removal/anti-redeposition agents, polymeric soil release agents, polymeric dispersing agents, polymeric grease cleaning agents, enzymes, enzyme stabilizing systems, bleaching compounds, bleaching agents, bleach activators, bleach catalysts, brighteners, dyes, hueing agents, dye transfer inhibiting agents, chelating agents, suds supressors, softeners, and perfumes.

Methods of Use

The present invention includes methods for cleaning soiled material. As will be appreciated by one skilled in the art, the cleaning compositions of the present invention are suited for use in laundry pretreatment applications, laundry cleaning applications, and home care applications.

Such methods include, but are not limited to, the steps of contacting cleaning compositions in neat form or diluted in wash liquor, with at least a portion of a soiled material and then optionally rinsing the soiled material. The soiled material may be subjected to a washing step prior to the optional rinsing step.

For use in laundry pretreatment applications, the method may include contacting the cleaning compositions described herein with soiled fabric. Following pretreatment, the soiled fabric may be laundered in a washing machine or otherwise rinsed.

Machine laundry methods may comprise treating soiled laundry with an aqueous wash solution in a washing machine having dissolved or dispensed therein an effective amount of a machine laundry cleaning composition in accord with the invention. An "effective amount" of the cleaning composition means from about 20 g to about 300 g of product dissolved or dispersed in a wash solution of volume from about 5 L to about 65 L. The water temperatures may range from about 5° C. to about 100° C. The water to soiled material (e.g., fabric) ratio may be from about 1:1 to about 20:1. In the context of a fabric laundry composition, usage levels may also vary depending not only on the type and severity of the soils and stains, but also on the wash water temperature, the volume of wash water, and the type of washing machine (e.g., top-loading, front-loading, top-loading, vertical-axis Japanese-type automatic washing machine).

The cleaning compositions herein may be used for laundering of fabrics at reduced wash temperatures. These methods of laundering fabric comprise the steps of delivering a laundry cleaning composition to water to form a wash liquor and adding a laundering fabric to said wash liquor, wherein the wash liquor has a temperature of above 0° C. to about 30° C., or to about 25° C., or to about 15° C. The fabric may be contacted to the water prior to, or after, or simultaneous with, contacting the laundry cleaning composition with water.

Another method includes contacting a nonwoven substrate impregnated with an embodiment of the cleaning composition with soiled material. As used herein, "nonwoven substrate" can comprise any conventionally fashioned nonwoven sheet or web having suitable basis weight, caliper (thickness), absorbency, and strength characteristics. Non-limiting examples of suitable commercially available nonwoven substrates include those marketed under the tradenames SON-TARA® by DuPont and POLYWEB® by James River Corp.

Hand washing methods, and combined handwashing with semiautomatic washing machines, are also included.

Machine Dishwashing Methods

Methods for machine-dishwashing or hand dishwashing soiled dishes, tableware, silverware, or other kitchenware, are included. One method for machine dishwashing comprises treating soiled dishes, tableware, silverware, or other kitchenware with an aqueous liquid having dissolved or dispensed therein an effective amount of a machine dishwashing composition in accord with the invention. By an effective amount of the machine dishwashing composition it is meant from about 8 g to about 60 g of product dissolved or dispersed in a wash solution of volume from about 3 L to about 10 L.

One method for hand dishwashing comprises dissolution of the cleaning composition into a receptacle containing water, followed by contacting soiled dishes, tableware, silverware, or other kitchenware with the dishwashing liquor, then hand scrubbing, wiping, or rinsing the soiled dishes, tableware, silverware, or other kitchenware. Another method for hand dishwashing comprises direct application of the cleaning composition onto soiled dishes, tableware, silverware, or other kitchenware, then hand scrubbing, wiping, or rinsing the soiled dishes, tableware, silverware, or other kitchenware. In some examples, an effective amount of cleaning composition for hand dishwashing is from about 0.5 ml. to about 20 ml. diluted in water.

Packaging for the Compositions

The cleaning compositions described herein can be packaged in any suitable container including those constructed from paper, cardboard, plastic materials, and any suitable laminates. An optional packaging type is described in European Application No. 94921505.7.

Multi-Compartment Pouch Additive

The cleaning compositions described herein may also be packaged as a multi-compartment cleaning composition.

SYNTHESIS EXAMPLES

In the examples, the following abbreviations are used:
BuO butylene oxide
PO propylene oxide Example 1: 1 Mole Glycerine+3 Mole BuO+3 Mole PO, Aminated a) 1 mole Glycerine+3 mole BuO+3 mole PO
In a 3.5 L autoclave 95.0 g glycerine and 1.0 g potassium tert.-butylate were mixed. The auto-clave was purged three times with nitrogen and heated to 140° C. 223.0 g butylene oxide was added within 90 minutes. The mixture was allowed to post-react for 5 hours at 140° C. Then, 179.7 g propylene oxide was added in portions within 1 hour. To complete the reaction, the mixture was allowed to post-react for additional 3 hours at 140° C. The reaction mixture was stripped with nitrogen and volatile compounds were removed in vacuo at 80° C. The catalyst was removed by adding 4.9 g synthetic magnesium silicate (Macrosorb MP5plus, Ineos Silicas Ltd.) stirring at 100° C. for 2 hours and filtration.

A yellowish oil was obtained (490.0 g, hydroxy value: 314.5 mgKOH/g).

b) 1 mole Glycerine+3 mole BuO+3 mole PO, aminated
In a 9 L autoclave 350 mL of the resulting triol mixture from example 1-a, 1200 mL THF and 1500 g ammonia were mixed in presence of 200 mL of a solid catalyst as described in EP0696572B1. The catalyst containing nickel, cobalt, copper, molybdenum and zirconium was in the form of 3×3 mm tablets. The autoclave was purged with hydrogen and the reaction was started by heating the autoclave. The reaction mixture was stirred for 15 h at 205° C., the total pressure was maintained at 280 bar by purging hydrogen during the entire reductive amination step. After cooling down the autoclave the final product was collected, filtered, vented of excess ammonia and stripped in a rotary evaporator to remove light amines and water. A total of 350-400 grams of a low-color etheramine mixture was recovered. The analytical results thereof are shown in Table 1.

TABLE 1

Analytical results of etheramine of example 1

| Total amine-value mg KOH/g | Total acetylatables mg KOH/g | Secondary and tertiary amine value mg KOH/g | Tertiary amine-value mg KOH/g | Hydroxyl value mg KOH/g | Grade of amination in % | Primary Amine in % of total amine |
|---|---|---|---|---|---|---|
| 352.30 | 357.43 | 3.43 | 0.75 | 5.88 | 98.77 | 99.03 |

Example 2: 1 Mole Glycerine+3 Mole PO+3 Mole BuO, Aminated a) 1 mole Glycerine+3 mole PO+3 mole BuO
In a 3.5 L autoclave 88.1 g glycerine and 0.9 g potassium tert.-butylate were mixed. The auto-clave was purged three times with nitrogen and heated to 140° C. 166.6 g propylene oxide was added within 1 hour. The mixture was allowed to post-react for 3 hours at 140° C. Then, 206.8 g butylene oxide was added in portions within 1 hours. To complete the reaction, the mixture was allowed to post-react for additional 3 hours at 140° C. The reaction mixture was stripped with nitrogen and volatile compounds were removed in vacua at 80° C. The catalyst was removed by adding 4.4 g Macrosorb MP5plus, stirring at 100° C. for 2 hours and filtration. A yellowish oil was obtained (410.0 g, hydroxy value: 336.5 mgKOH/g).

b) 1 mole Glycerine+3 mole PO+3 mole BuO, aminated
In a 9 L autoclave 350 mL of the resulting triol mixture from example 2-a, 1200 mL THF and 1500 g Ammonia were mixed in presence of 200 mL of a solid catalyst as described in EP0696572B1. The catalyst containing nickel, cobalt, copper, molybdenum and zirconium was in the form of 3×3 mm tablets. The autoclave was purged with hydrogen and the reaction was started by heating the autoclave. The reaction mixture was stirred for 15 h at 205° C., the total pressure was maintained at 280 bar by purging hydrogen during the entire reductive amination step. After cooling down the autoclave the final product was collected, filtered, vented of excess ammonia and stripped in a rotary evaporator to remove light amines and water. A total of 300-350 grams of a low-color etheramine mixture was recovered. The analytical results thereof are shown in Table 2.

TABLE 2

Analytical results of etheramine of example 2

| Total amine-value mg KOH/g | Total acetylatables mg KOH/g | Secondary and tertiary amine value mg KOH/g | Tertiary amine-value mg KOH /g | Hydroxyl value mg KOH/g | Grade of amination in % | Primary Amine in % of total amine |
|---|---|---|---|---|---|---|
| 373.88 | 377.50 | 1.33 | 0.66 | 4.28 | 99.21 | 99.64 |

Example 3: 1 Mole Glycerine+6 Mole BuO, Aminated a) 1 mole Glycerine+6 mole BuO In a 3.5 L autoclave 103.4 g glycerine and 1.2 g potassium tert-butylate were mixed. The auto-clave was purged three times with nitrogen and heated to 140° C. 485.5 g butylene oxide was added within 2 hours. To complete the reaction, the mixture was allowed to post-react for additional 7 hours at 140° C. The reaction mixture was stripped with nitrogen and volatile compounds were removed in vacuo at 80° C. The catalyst was removed by adding 5.9 g Macrosorb MP5plus, stirring at 100° C. for 2 hours and filtration.

A yellowish oil was obtained (589.0 g, hydroxy value: 285.0 mgKOH/g).

a) Glycerine+6 mole BuO, aminated

In a 9 L autoclave 500 g of the resulting triol mixture from example 3-a, 1200 mL THF and 1500 g Ammonia were mixed in presence of 200 mL of a solid catalyst as described in EP0696572B1. The catalyst containing nickel, cobalt, copper, molybdenum and zirconium was in the form of 3×3 mm tablets. The autoclave was purged with hydrogen and the reaction was started by heating the autoclave. The reaction mixture was stirred for 15 h at 205° C., the total pressure was maintained at 280 bar by purging hydrogen during the entire reductive amination step. After cooling down the autoclave the final product was collected, filtered, vented of excess ammonia and stripped in a rotary evaporator to remove light amines and water. A total of 450 grams of a low-color etheramine mixture was recovered. The analytical results thereof are shown in Table 3.

Example 4: 1 Mole Glycerine+4.2 Mole PO+1.8 Mole BuO, Aminated a) 1 mole Glycerine+4.2 mole PO+1.8 mole BuO In a 3.5 L autoclave 88.9 g glycerine and 0.9 g potassium tert.-butylate were mixed. The auto-clave was purged three times with nitrogen and heated to 140° C. 235.4 g propylene oxide was added within 1.5 hour. The mixture was allowed to post-react for 3 hours at 140° C. Then, 125.2 g butylene oxide was added in portions within 1 hour. To complete the reaction, the mixture was allowed to post-react for additional 5 hours at 140° C. The reaction mixture was stripped with nitrogen and volatile compounds were removed in vacuo at 80° C. The catalyst was removed by adding 4.7 g Macrosorb MP5plus, stirring at 100° C. for 2 hours and filtration.

A yellowish oil was obtained (470.0 g, hydroxy value: 312.1 mgKOH/g).

b) 1 mole Glycerine+4.2 mole PO+1.8 mole BuO, aminated

In a 9 L autoclave 350 mL of the resulting triol mixture from example 4-a, 1200 mL THF and 1500 g Ammonia were mixed in presence of 200 mL of a solid catalyst as described in EP0696572B1. The catalyst containing nickel, cobalt, copper, molybdenum and zirconium was in the form of 3×3 mm tablets. The autoclave was purged with hydrogen and the reaction was started by heating the autoclave. The reaction mixture was stirred for 15 h at 205° C., the total pressure was maintained at 280 bar by purging hydrogen during the entire reductive amination step. After cooling down the autoclave the final product was collected, filtered, vented of excess ammonia and stripped in a rotary evaporator to remove light amines and water. A total of 350-400 grams of a low-color etheramine mixture was recovered. The analytical results thereof are shown in Table 4.

TABLE 3

Analytical results of etheramine of example 3.

| Total amine-value mg KOH/g | Total acetylatables mg KOH/g | Secondary and tertiary amine value mg KOH/g | Tertiary amine-value mg KOH/g | Hydroxyl value mg KOH/g | Grade of amination in % | Primary Amine in % of total amine |
|---|---|---|---|---|---|---|
| 313.30 | 327.30 | 1.54 | 0.22 | 14.22 | 95.66 | 99.51 |

TABLE 4

Analytical results of etheramine of example 4.

| Total amine-value mg KOH/g | Total acetylatables mg KOH/g | Secondary and tertiary amine value mg KOH/g | Tertiary amine-value mg KOH/g | Hydroxyl value mg KOH/g | Grade of amination in % | Primary Amine in % of total amine |
|---|---|---|---|---|---|---|
| 343.96 | 347.12 | 3.26 | 0.76 | 3.92 | 99.31 | 99.05 |

Example 5 (Comparative): 1 Mole Glycerine+6 Mole PO, Aminated a) 1 mole Glycerine+6 mole PO In a 2 L autoclave 276.3 g glycerine and 2.6 g potassium tert.-butylate were mixed. The auto-clave was purged three times with nitrogen and heated to 140° C. 1044.0 g propylene oxide was added within 10 hours. The mixture was allowed to post-react for 9.5 hours at 140° C. The reaction mixture was stripped with nitrogen and volatile compounds were removed in vacuo at 80° C. The catalyst was removed by adding 21.1 g Macrosorb MP5plus, stirring at 100° C. for 2 hours and filtration.

A light yellow oil was obtained (1300.0 g, hydroxy value: 320.2 mgKOH/g).

b) 1 mole Glycerine+6 mole PO, aminated

In a 9 L autoclave 750 mL of the resulting polyol mixture from example 5-a, 1000 mL THF and 1500 g ammonia were mixed in presence of 200 mL of a solid catalyst as described in EP0696572B1. The catalyst containing was nickel, cobalt, copper, molybdenum and zirconium was in the form of 3×3 mm tablets. The autoclave was purged with hydrogen and the reaction was started by heating the autoclave. The reaction mixture was stirred for 15 h at 205° C., the total pressure was maintained at 250 bar by purging hydrogen during the entire reductive amination step. After cooling down the autoclave the final product was collected, filtered, vented of excess ammonia and stripped in a rotary evaporator to remove light amines and water. 720 g of a low-color etheramine mixture was recovered. The analytical results thereof are shown in Table 5.

TABLE 5

| Total amine-value mg KOH/g | Total acetylatables mg KOH/g | Secondary and tertiary amine value mg KOH/g | Tertiary amine-value mg KOH/g | Hydroxyl value mg KOH/g | Grade of amination in % | Primary Amine in % of total amine |
|---|---|---|---|---|---|---|
| 368.70 | 380.00 | 2.85 | 0.00 | 11.30 | 97.03 | 99.23 |

Use as Additives in Laundry Detergents

Technical stain swatches of blue knitted cotton containing Beef Fat, Pork Fat, Sausage Fat, Bacon Grease and Anchor Butter were purchased from Warwick Equest Ltd. and washed in conventional western European washing machines (Miele Waschmaschine Softronic W 2241), selecting a 59 min washing cycle without heating (wash at 18° C.) and using 75 g of liquid detergent composition LA1 (table 8) together with or without 1.25 g of etheramine additive and some hydrochloric acid to readjust the pH after addition of the etheramine. Water hardness was 2.5 mM ($Ca^{2+}$: $Mg^{2+}$ was 3:1). Standard colorimetric measurement was used to obtain L*, a* and b* values for each stain before and after the washing. From L*, a* and b* values the stain level was calculated.

Stain removal from the swatches was calculated as follows:

Stain Removal Index (SRI)=$(\Delta E_{initial} - \Delta E_{washed})*100/\Delta E_{initial}$ $\Delta E_{initial}$=Stain level before washing
$\Delta E_{washed}$ Stain level after washing Six replicates for each stain type have been carried out. Given below are the averaged values. Stain level corresponds to the amount of grease on the fabric. The stain level of the fabric before the washing ($\Delta E_{initial}$) is high, in the washing process stains are diminished and the stain level after washing is smaller ($\Delta E_{washed}$). The better the stains have been removed the lower the value for $\Delta E_{washed}$ will be and the higher the difference will be to $\Delta E_{initial}$. Therefore the value of stain removal index increases with better washing performance.

TABLE 8 liquid detergent composition LA1

| Ingredients of liquid detergent composition LA1 | percentage by weight |
|---|---|
| Alkyl Benzene sulfonate[1] | 7.50% |
| AE3S[2] | 2.60% |
| AE9[3] | 0.40% |
| NI 45-7[4] | 4.40% |
| Citric Acid | 3.20% |
| C1218 Fatty acid | 3.10% |
| Amphiphilic polymer[5] | 0.50% |
| Zwitterionic dispersant[6] | 1.00% |
| Ethoxylated Polyethyleneimine[7] | 1.51% |
| Protease[8] | 0.89% |
| Enymes[9] | 0.21% |
| Chelant[10] | 0.28% |
| Brightener[11] | 0.09% |
| Solvent | 7.35% |
| Sodium Hydroxide | 3.70% |

TABLE 8-continued liquid detergent composition LA1

| Ingredients of liquid detergent composition LA1 | percentage by weight |
|---|---|
| Fragrance & Dyes | 1.54% |
| Water, filler, stucturant | To Balance |

[1] Linear alkylbenenesulfonate having an average aliphatic carbon chain length C11-C12 supplied by Stepan, Northfield Illinois, USA
[2] AE3S is C12-15 alkyl ethoxy (3) sulfate supplied by Stepan, Northfield, Illinois, USA
[3] AE9 is C12-14 alcohol ethoxylate, with an average degree of ethoxylation of 9, supplied by Huntsman, Salt Lake City, Utah, USA
[4] NI 45-7 is C14-15 alcohol ethoxylate, with an average degree of ethoxylation of 7, supplied by Huntsman, Salt Lake City, Utah, USA
[5] Random graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units.
[6] A compound having the following general structure; bis((C2H5O)(C2H4O)n)(CH3)—N+—CxH2x—N+—(CH3)—bis((C2H5O)(C2H4O)n), wherein n = from 20 to 30, and x = from 3 to 8, or sulphated or sulphonated variants thereof
[7] Polyethyleneimine (MW = 600) with 20 ethoxylate groups per —NH
[8] Proteases may be supplied by Genencor International, Palo Alto, California, USA (e.g. Purafect Prime ®) or by Novozymes, Bagsvaerd, Denmark (e.g. Liquanase ®, Coronase ®).
[9] Natalase ®, Mannaway ® are all products of Novozymes, Bagsvaerd, Denmark.
[10] Suitable chelants are, for example, diethylenetetraamine pentaacetic acid (DTPA) supplied by Dow Chemical, Midland, Michigan, USA or Hydroxyethane di phosphonate (HEDP) or diethylene triamine penta(methyl phosphonic) acid supplied by Solutia, St Louis, Missouri, USA;
[11] Fluorescent Brightener 1 is Tinopal ® AMS, Fluorescent Brightener 2 supplied by Ciba Specialty Chemicals, Basel, Switzerland

TABLE 9

| | results | | | |
|---|---|---|---|---|
| Stain | A | B | C | D |
| Beef Fat | 75.3 | 80.2 | 78.8 | 75.1 |
| Pork Fat | 70.2 | 77.7 | 77.7 | 72.7 |
| Sausage Fat | 72.9 | 79.5 | 77.0 | 75.9 |
| Bacon Grease | 74.5 | 79.1 | 80.3 | 75.3 |
| Anchor Butter | 60.6 | 69.1 | 66.9 | 63.6 |

A: liquid detergent composition LA1 (table 8) without additional etheramine additive
B: liquid detergent composition LA1 (table 8) with the etheramine described in Example 1 (1 mole Glycerine + 3 mole BuO + 3 mole PO, aminated)
C: liquid detergent composition LA1 (table 8) with the etheramine described in Example 3 (1 mole Glycerine + 6 mole BuO, aminated)
D: liquid detergent composition LA1 (table 8) with the etheramine described in comparitive Example 5 (1 mole Glycerine + 6 mole PO, aminated)

All three etheramines in the test have a molecular ratio of alkylene oxide:glycerol of 6:1. For all the five grease stains a superior cleaning effect of the butylene-oxide containing etheramines (B and C) over the non-butylene oxide containing etheramine (D) and over the liquid detergent composition without etheramine (A) is seen.

The invention claimed is:

1. An etheramine of formula (I),

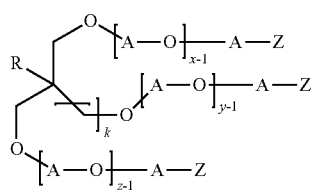

Formula (I)

wherein
R=H or ethyl, k=0 or 1
A represents a linear or branched alkylene group having $C_2$-$C_{18}$ carbon atoms,
A may be the same as or different from one another,
at least one A represents a linear or branched $C_4$-alkylene group,
the sum of x, y and z lies in the range of 5 to 10,
$x \geq 1$, $y \geq 1$ and $z \geq 1$,
Z=NH2 or OH but at least two Z per molecule are $NH_2$.

2. The etheramine according to claim 1, wherein at least three A represent a linear or branched $C_4$-alkylene group.

3. The etheramine according to claim 1, wherein all A groups represent a linear or branched $C_4$-alkylene group.

4. The etheramine according to claim 1, wherein Z is $NH_2$.

5. The etheramine according to claim 1, wherein the etheramine of formula (I) is reacted with an acid.

6. A process for the manufacture of an etheramine of formula (I)

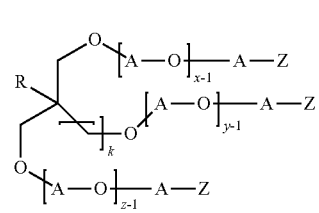

Formula (I)

wherein
R=H or ethyl, k=0 or 1
A represents a linear or branched alkylene group having $C_2$-$C_{18}$ carbon atoms,
A may be the same as or different from one another,
at least one A represents a linear or branched $C_4$-alkylene group,
the sum of x, y and z lies in the range of 5 to 10,
$x \geq 1$, $y \geq 1$ and $z \geq 1$,
Z=NH2 or OH but at least two Z per molecule are $NH_2$, comprising the following steps:
a) reacting glycerine or 1,1,1-trimethylolpropane with $C_4$-alkylene oxide and optionally with $C_2$-$C_{18}$ alkylene oxide, wherein the molar ratio of glycerine or 1,1,1-trimethylolpropane to $C_4$ alkylene oxide is in the range of 1:3 to 1:10, and
b) aminating the alkoxylated glycerine or alkoxylated 1,1,1-trimethylolpropane with ammonia.

7. The process according to claim 6, wherein the molar ratio of glycerine or 1,1,1-trimethylolpropane to $C_4$ alkylene oxide is in the range of 1:3 to 1:6.

8. The process according to claim 6, wherein the $C_2$-$C_{18}$ alkylene oxide is ethylene oxide, propylene oxide or a mixture thereof.

9. The process according to claim 6, wherein the amination is carried out in the presence of copper-, nickel- or cobalt-containing catalyst.

10. The process according to claim 6, wherein the catalytically active material of the catalysts, before the reduction thereof with hydrogen, comprises oxygen compounds of aluminum, of copper, of nickel and of cobalt, and is in the range from 0.2 to 5.0% by weight of oxygen compounds of tin, calculated as SnO.

11. A personal care product which comprises the polyetheramine of claim 1.

12. A shampoo and body wash formulation which comprises the polyetheramine of claim 1.

13. A curing agent for epoxy resins or as a reactant in the production of polymers which comprises the polyetheramine of claim 1.

14. A polyurethane, polyurea, or a thermoplastic polyamide adhesive which comprises the polyetheramine of claim 1.

* * * * *